United States Patent [19]

Kocal

[11] Patent Number: 4,835,333
[45] Date of Patent: May 30, 1989

[54] MOTOR FUEL ALKYLATION PROCESS UTILIZING A SURFACTANT CONTAINING CATALYST TO REDUCE HYDROFLUORIC ACID REQUIREMENTS

[75] Inventor: Joseph A. Kocal, Gurnee, Ill.

[73] Assignee: UOP, Des Plaines, Ill.

[21] Appl. No.: 223,310

[22] Filed: Jul. 25, 1988

Related U.S. Application Data

[62] Division of Ser. No. 68,513, Jul. 1, 1987, Pat. No. 4,795,728.

[51] Int. Cl.$^4$ ................................................ C07C 2/58
[52] U.S. Cl. .................................... 585/724; 585/725
[58] Field of Search ................................ 585/724, 725

[56] References Cited

U.S. PATENT DOCUMENTS 3,364,280  1/1968  Kramer ............................... 585/725
3,870,765  3/1975  McCoy et al. ....................... 585/725

Primary Examiner—Curtis R. Davis
Attorney, Agent, or Firm—Thomas K. McBride; John F. Spears, Jr.; A. Blair Hughes

[57] ABSTRACT

A novel hydrofluoric acid-catalyzed motor fuel alkylation process and catalyst is disclosed which incorporates from 0.5 to 5 vol. % of a cationic or anionic surfactant component in an HF containing acid alkylation catalyst to enable the process to be operated at an olefin-to-acid volumetric feed ratio greater than 1.0 while producing a motor alkylate product with a good octane number.

5 Claims, No Drawings

MOTOR FUEL ALKYLATION PROCESS UTILIZING A SURFACTANT CONTAINING CATALYST TO REDUCE HYDROFLUORIC ACID REQUIREMENTS

CROSS-REFERENCE TO RELATED APPLICATION

This application is a Divisional application of prior copending application Ser. No. 068,513 filed July 1, 1987, now U.S. Pat. No. 4,795,728.

BACKGROUND OF THE INVENTION

This invention relates to an improved process and catalyst for the alkylation of an isoparaffin with an olefin-acting agent. Specifically, the invention relates to a hydrofluoric acid alkylation process which utilizes an acid catalyst containing a cationic or anionic surfactant component along with hydrofluoric acid to improve the solubility of an isoparaffin in the acid catalyst and thus allows the process to utilize a reduced amount of dangerous hydrofluoric acid containing catalyst while maintaining product quality.

Alkylation of isoparaffinic hydrocarbons, such as isobutane and isopentane, with olefinic hydrocarbons such as propylene, butylene and amylenes or with other olefin-acting agents such as $C_3$–$C_5$ alkylhaides, etc., using mineral acids such as hydrogen fluoride is well known as a commercially important method for producing gasoline boiling range hydrocarbons. The $C_5$–$C_{10}$ hydrocarbons typically produced in isoparaffin-olefin alkylation operations are termed "alkylate". Alkylate is particularly useful as a motor fuel blending stock. It possesses motor and research octane ratings high enough that it may be employed to improve overall octane ratings of available gasoline pools in order to provide motor fuels which comply with the requirements of modern automobile motors. High octane alkylate blending components are particularly important in producing motor fuels of sufficiently high octane since it is now mandatory to avoid use of alkyl lead antiknock compounds in gasoline. A continuing goal in the art is to provide an economically attractive and intrinsically safe acid-catalyzed alkylation process.

Maximizing alkylate octane while providing the safest possible process is a sometimes difficult feat. The goal of mazimizing alkylate octane takes on new significance with the recent phaseout of alkyl lead antiknock compounds as blending agents for gasoline as mandated by government regulation. Additionally, the government and society in general are becoming increasingly aware and apprehensive about the manufacture, use, and disposal of toxic chemicals. Hydrofluoric acid poses a definite health and environmental risk as it is extremely corrosive and therefore a potential health hazard. The minimization of the use of hydrofluoric acid in an alkylation process is therefore quite desirable.

In commercial isoparaffin-olefin alkylation operations using acid catalysts, generally, isobutane is the isoparaffin used and propylene, butylene and amylenes or a mixture of these olefins, are used as the olefin-acting agent. Typically, the acid catalyst will comprise hydrogen fluoride. In conventional operations, the isoparaffin, olefin-acting agent and hydrogen fluoride catalyst are first contacted and thoroughly admixed in an alkylation reactor, forming a reaction mixture, or emulsion. After a relatively short time, the alkylation reaction is substantially complete and the reaction mixture is withdrawn from the alkylation reactor and is allowed to settle by gravity into immiscible hydrocarbon and catalyst phases in a settling vessel. The hydrogen fluoride catalyst phase thus separated is returned to the alkylation reactor for further catalytic use. The hydrocarbon phase separated in the settling operation is further processed, e.g., by fractionation, to recover an alkylate product and to separate unconsumed isoparaffin for recycle to the alkylation reactor. The recovered alkylate product may then be added to the motor fuel octane pool as a blending component. It is, therefore, desirable that the alkylate product has as high a research octane number as possible.

OBJECTS AND EMBODIMENTS

It is therefore an object of the present invention to provide an improved process and catalyst for the hydrofluoric acid-catalyzed alkylation of an isoparaffin with an olefin-acting agent by producing an alkylate having good antiknock properties while minimizing hydrofluoric acid catalyst requirements.

Accordingly, the present invention is a process for the alkylation of an isoparaffin with an olefin-acting agent comprising contacting the isoparaffin with an olefin-acting agent at alkylation conditions including an olefin to acid catalyst space velocity greater than about 1.0. The process utilizes a novel acid catalyst comprising an anhydrous mixture of from about 0.5 to 5 vol.% of a cationic or anionic surfactant component and preferably a cationic or anionic surfactant component containing $C_7$ or smaller aliphatic or aromatic substituted components along with from about 95 to 99.5 vol.% of a hydrofluoric acid component.

This as well as other objects and embodiments will become apparent upon review of the following more detailed description of the prior art and the invention.

INFORMATION DISCLOSURE

The art is familiar with the use of acid catalyst modifiers in the process of alkylating an isoparaffin with an olefin in order to increase product quality and reaction efficiency. U.S. Pat. No. 4,634,801 describes a process which utilizes an ether component additive in an alkylation process for the purpose of improving the acid-to-hydrocarbon ratio of the combined reactants while maintaining product quality. In a similar disclosure, U.S. Pat. No. 4,180,691 describes the use of a surfactant in the acid-catalyzed alkylation of an aromatic component with a monoolefin. The addition of the surfactant reduces the content of undesirable 2-phenyl isomers in the product. In addition to using an anionic surfactant, the invention disclosed in the U.S. Pat. No. 4,180,691 is distinguished from that of the present invention in that the hydrocarbon feed being alkylated consists of in part an aromatic compound, and no increase in the hydrocarbon-to-acid volumetric feed ratio is contemplated.

U.S. Pat. No. 3,324,196 discloses the addition of very small quantities of amines into the process stream of a motor fuel alkylation process in order to reduce acid consumption and prevent the formation of an emulsion. While this disclosure is partially related to the use of amines as a hydrofluoric acid alkylation catalyst modifier, the benefits of the amine addition were proven only in a sulfuric acid system. For example, acid consumption in a hydrofluoric acid-catalyzed alkylation process is not a problem as the acid remains almost refractory throughout the process. Inefficient recovery of the hydrofluoric acid for reuse would be the prime cause of acid consumption in such a process. The formation of an emulsion as disclosed as a problem in the U.S. Pat. No. 3,324,196 would also only be a problem in the aqueous sulfuric acid alkylation process. A hydrofluoric acid-catalyzed alkylation process is inherently anhydrous. The addition of non-aqueous additives would not be expected to cause an emulsion to form at higher catalyst additive levels. In fact, the surfactant addition levels disclosed in the instant invention as being most desirable range from 0.5 to 5.0 vol.% of the hydrofluoric acid/-surfactant mixture. This is much higher than the 0.0005 to 0.3 wt.% amine addition range disclosed in the U.S. Pat. No. 3,324,196.

U.S. Pat. No. 3,364,280 is very similar to the U.S. Pat. No. 3,324,196 in the limitation of the amount of modifier added to promote a motor fuel alkylation reaction. The U.S. Pat. No. 3,364,280 discloses the use of from 0.0005 to 0.2 wt.% based upon acid weight of an aliphatic sulfonium or phosphonium salts. The benefits of adding such limited amounts of surfactants to an alkylation process are also identical to the benefits listed in the U.S. Pat. No. 3,324,196, namely, reduced acid consumption and avoidance of a problem product emulsion. The process of the instant invention is distinguished from the U.S. Pat. No. 3,364,280 for most of the same reasons it is different from the U.S. Pat. No. 3,364,280. To reiterate, the U.S. Pat. No. 3,364,280 describes improvements in acid consumption and the avoidance of a problem emulsion in an alkylation process by the addition of very small quantities of specific surfactants to an acid-catalyzed alkylation process. The U.S. Pat. No. 3,364,280 claims similar improvements in hydrofluoric alkylation process while disclosing examples only of improvements to sulfuric acid alkylation process. As mentioned previously, the nature of the hydrofluoric acid alkylation process is such that the improvements disclosed in the U.S. Pat. No. 3,364,280 would not be necessary in an HF alkylation process because acid consumption and emulsions are not problems encountered in HF alkylation. Additionally, the process of the present invention utilizes a larger volume of cationic surfactants than claimed in the to reduce the HF acid requirements in an HF alkylation process, a benefit not foreseen in the prior art.

U.S. Pat. No. 3,231,633 describes a motor fuel alkylation process which employs a carbonium ion-forming triphenylmethyl salt or tricyclopropylmethyl salt to reduce the reaction induction period or, in other words, the additive speeds up the formation of the necessary 1:1 olefin-paraffin adduct. The U.S. Pat. No. 3,231,633 broadly covers the addition of from 0.01 to 10 mole percent of the above salt to an alkylation process operating at a wide range of conditions. The U.S. Pat. No. 3,231,633 is silent to the benefits of operating the process at increased olefin-to-acid feed ratios. In fact, while disclosing a potential olefin-to-acid feed ratio range of from 0.01 to 20 in column 4, lines 41–42, the reaction conditions utilized in the examples incorporated an olefin to acid space velocity of 0.035 to 0.065 v/hr/v. This range actually utilized in the examples is well below the 0.5 v/hr/v disclosed in the instant invention.

In summary, the art has previously disclosed the use of modifiers including specific surfactants to improve various process and product aspects of motor fuel alkylation processes. The art however has not detail the surprising reduction in acid circulation rate and thus acid inventory achieved by the addition of specific cationic or anionic surfactant containing HF alkylation catalyst to a paraffin olefin alkylation process.

DETAILED DESCRIPTION OF THE INVENTION

To reiterate briefly, the present invention relates to a process and catalyst for the acid-catalyzed alkylation of an isoparaffin with an olefin-acting agent comprising contacting the isoparaffin with the olefin-acting agent at alkylation conditions including an olefin to acid catalyst space velocity greater than about 0.5. The process utilizes an acid catalyst comprising an anhydrous, nonalcoholic mixture of from about 0.5 to 5.0 vol.% of a cationic or anionic surfactant along with from about 95 to 99.5 vol.% of a hydrofluoric acid component.

As heretofore indicated, the process of the instant invention is for the alkylation of an isoparaffin with an olefin-acting agent. Typical of the isoparaffins which may be utilized in the invention are isobutane, isopentane and similar isoparaffins. The preferred isoparaffins are isobutane and isopentane, particularly, isobutane. A mixture of two or more isoparaffins may also be employed, if desired. Conventional isobutane alkylation feedstocks are suitable for use in the present process. Such conventional isobutane feedstocks may contain some nonreactive hydrocarbons such as normal paraffins. For example, a conventional commercial isobutane alkylation feedstock generally contains about 95 wt.% isobutane, 4 wt.% normal butane, and 1 wt.% propane.

Olefin-acting agents which are suitable for use in the process of the present invention include $C_3$–$C_6$ monoolefins, alkylhalides, or mixtures thereof. $C_3$–$C_5$ olefins are preferred. The process of the present invention may be applied to the alkylation of mixtures of two or more olefin-acting agents with the same benefits and improvements as would be obtained in using a single olefin-acting agent. For example, many conventional olefin feedstocks utilized in commercial alkylation operation contain mixtures of propylene and butylenes, or propylene, butylenes and amylenes. Application of the present process to such olefin mixtures results in improvements in quality of the products obtained which are equal to the improvement obtained using a single olefin. Similarly, a mixture of $C_3$–$C_5$ alkylhalides and olefins in any proportion is also suitable in many cases, for example, when the halide is fluoride. The particularly preferred $C_3$–$C_5$ olefin feedstocks are conventionally derived from petroleum refining processes such as catalytic cracking and may contain substantial amounts of paraffins, lighter and heavier olefins, etc. Olefin feedstocks derived from such conventional sources are suitable for use in providing the olefin-acting compound used in the present process.

It is contemplated that the process disclosed herein would also be useful in the alkylation reactions of other alkylatable hydrocarbons which have been alkylated in HF acid alkylation processes. Such reactions might include the alkylation of aromatics with long chain olefins to produce linear alkylbenzenes or the alkylation of aromatics with olefins such as ethylene or propylene to product ethylbenzene or cumene.

As heretofore indicated, the novel acid catalyst used in the process of the present invention comprises an anhydrous mixture of hydrofluoric acid and a cationic or anionic surfactant. It should be understood that by the term "anhydrous", it is meant that the water content of the acid catalyst should comprise no more than about 3 wt.% based upon the total weight of the acid catalyst phase. The presence of water in the acid catalyst phase greatly increases the corrosive properties of the hydrofluoric acid and can be detrimental to process materials of construction. Additionally, the mixture of HF acid and cationic or anionic surfactant contained in the acid catalyst is homogeneous, forming a single liquid phase.

Hydrofluoric acid is the acid component of the acid catalyst of the instant process because it is one of the most stable mineral acids. It can be subjected to high temperatures and pressures and to the action of other catalytic agents without being broken down. Many of its organic compounds decompose either by heat alone or in the presence of catalyst to regenerate hydrofluoric acid. This results in an extremely low catalyst consumption in the process. In fact, HF acid is consumed in the process in only minute amounts through the production of alkylfluorides which are recovered and neutralized as process by-products. An important advantage of using hydrofluoric acid as a component of the acid catalyst is that by virtue of its chemical stability and low freezing point, it may be employed over a wide range of operating conditions. Conditions may be employed which are most satisfactory thermodynamically or economically, without limitations due to catalyst physical properties. For example, in the alkylation reaction, ambient or slightly superambient temperatures may be used with hydrofluoric acid. Hence, it is unnecessary to utilize refrigeration as might be the case when certain other mineral acids are utilized as the alkylation catalysts. The vapor pressure of hydrofluoric acid makes it unnecessary to resort to extreme pressure to maintain the catalyst in liquid phase. Its freezing point permits its use at temperatures much lower than is possible with most catalysts which either freeze or become highly viscous at low temperatures. Although in the alkylation of isobutane with olefins to produce aviation blending fuel, the usual operating conditions are of the order of about 30° C., there are catalytic reactions which are favored by lower temperatures. Since hydrofluoric acid catalyzes such reactions, it is a distinct advantage because of its physical properties. Conversely, since hydrofluoric acid is thermally stable, it can be employed at much higher temperatures than other alkylation catalysts. This is a unique property of hydrofluoric acid.

As previously indicated, the acid catalyst of the present invention comprises from about 95 to about 99.5 vol.% hydrofluoric acid based upon the total weight of the acid catalyst. The remaining 0.5 to about 5 wt.% of the acid catalyst is comprised of a cationic or anionic surfactant component.

The second component of the acid catalyst is the cationic or anionic surfactant component. The cationic or anionic surfactant component is an integral part of the acid catalyst as it allows the process to be operated at reduced catalyst acid rates while maintaining good product octane values. The tremendously large number of compounds which may be characterized as surfactants has prevented the development of a definitive characterization of this group of compounds. As used herein, the term "surfactant" is intended to indicate a compound which satisfies the six fundamental characteristics set out on page 507 of Volume 19 of *Kirk-Othmer Encyclopedia of Chemical Technology*, 2nd Edition, Interscience Publishers, 1969. These six fundamental characteristics include solubility in at least one phase of a liquid system, an amphipathic structure, the tendency to form oriented monolayers at phase interfaces, preferential equilibrium concentration at a phase interface as compared to the bulk of a solution, micelle formation, and the possession of some combination of the functional properties of surfactants, which include detergency, foaming, wetting, emulsifying, solubilizing, and dispersing.

Surfactants are classified as being cationic, anionic, or neutral depending on their solubilized charge. Preferably, the surfactant of the instant invention is a cationic or anionic surfactant. A cationic surfactant is one that exhibits a positive charge when solubilized. Conversely, an anionic surfactant is one that exhibits a negative charge when solubilized. Additionally, the preferred cationic or anionic surfactant is a hydrophilic material which is soluble in the acid catalyst phase of the two phase alkylation reaction system. It is believed that the cationic and anionic surfactants are most useful in the instant process because they optimally increase the solubility of the primary reactant isobutane in the acid phase of an acid-catalyzed alkylation process. The increase in the isobutane HF acid solubility created by the preferred sufactant allows the HF acid concentration to be reduced in order to return the process to similar reaction mixture levels of isobutane in the HF acid.

It is preferred that the cationic or anionic surfactant utilized in the acid catalyst of the instant invention be comprised of a small, stable cationic surfactant. By "small", it is meant a cationic surfactant containing only aliphatic or aromatic substituted organic compounds of 10 carbon atoms or smaller and preferably 7 carbon atoms or smaller.

It is also preferred that the cationic or anionic surfactant component of the acid catalyst contain a sulfur or a phosphorus component. Cationic and anionic surfactants containing such components have been found to be very effective as a portion of the acid catalyst of the instant invention. In the case a cationic surfactant is used as a portion of the acid catalyst of the instant invention, the preferred sulfur and phosphorus components in the cationic surfactant will take the form of sulfonium or phosphonium salts. These salts will have the general structure:

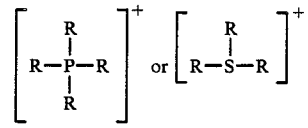

where R is an aliphatic or aromatic compound of 10 carbon atoms or less and preferably of 7 carbon atoms or less.

It is preferred that the small, stable cationic surfactant of the instant invention is tetrabutylphosphonium bromine.

As previously mentioned, the preferred anionic surfactant used as a portion of the novel acid catalyst in the instant alkylation process preferably contains a sulfur or phosphorus compound. Such components in an anionic surfactant will typically take the form of a sulfonic or phosphonic compound. Sulfur containing or sulfonic anionic surfactants may be present as: sulfates and sulfated compounds like sulfated esters, sulfated alkanolamides, alkyl sulfates and the like, or as sulfonates with the formula $R-SO_3^-$ where R may be an aliphatic compound, aromatic, alkylaromatic, naphthalene, an olefin and other similar hydrocarbon compounds.

Phosphorus containing or phosphonic anionic surfactants useful in the acid catalyst of the instant invention include alkylphosphates, alkylpolyphosphates, phosphate mono- and diesters of the formulae:

R—$(OCH_2CH_2)_4OPO_3H^-$-monoester;

$(R(OCH_2CH_2)_4)_2PO_2^-$-diester and the like phosphorus containing anionic surfactants.

It is preferred that the hydrocarbon group components represented by the symbol R in the formulae above comprise aliphatic or aromatic compounds of 10 or less carbon atoms and preferably 7 or less carbon atoms.

It is most preferred that the anionic surfactant of the instant invention is diisobutylthiophosphinate.

It is an aspect of the instant invention that the surfactant component of the instant catalyst may contain a mixture of both an anionic and cationic surfactant. Additionally, the cationic or anionic surfactant of the instant invention as previously noted should be soluble in the HF acid portion of the acid catalyst and therefore becomes a constituent of the hydrofluoric acid containing catalyst. The desired surfactant component is recoverable as a portion of the acid catalyst in the acid catalyst separation zone. However, in the catalyst regeneration zone, a small portion of the surfactant is separated from the HF acid by fractionation and typically removed from the process as a portion of a heavy by-product stream. However, as mentioned, this lost surfactant portion is typically only a very small portion of the total process inventory of surfactant and therefore the anticipated surfactant make-up requirements are expected to be small.

As heretofore indicated, an object of the present invention is the production of a high octane alkylate by means of an acid-catalyzed alkylation of an isoparaffin with an olefin-acting agent wherein the process has much lower acid requirements. It has been discovered that utilizing an alkylation catalyst comprising an anhydrous mixture of from about 95 to 99.5 vol.% hydrofluoric acid and from about 0.5 to 5.0 vol.% of a cationic surfactant component allows for lower acid requirements than the prior art alkylation process while still maintaining the same octane properties of the alkylate. Accordingly, the amount of acid catalyst utilized in the present invention is sufficient such that the volumetric ratio of olefin-acting agent to acid catalyst being fed into the reaction zone is greater than about 0.5, and preferably greater than 1.0. In contradistinction, prior art processes typically employ alkylation catalysts in an amount at least 10 to 20 times greater than that of the present invention such that the volumetric ratio of olefinacting agent to hydrofluoric acid is 0.1 or less and as low as 0.05 or less. As will be hereinafter demonstrated, the use of a novel acid catalyst allows the production of high quality alkylate using much less HF acid than in prior art processes.

As will be readily apparent to one of ordinary skill in the art, it is very desirable to minimize use of mineral acid in the alkylation process. For example, as indicated heretofore, the desired mineral acid employed in the instant alkylation process is hydrogen fluoride. The corrosive properties of HF acid are of course well known in the art. Use of HF as an alkylation catalyst therefore necessitates use of processing equipment employing exotic and expensive alloys such as monel, hastalloy, etc. By minimizing the HF requirements of a process, it is contemplated that there will be a commensurate minimization of the use of such alloys. More importantly, as will be recognized by those of ordinary skill in the art, it is extremely advantageous to minimize the use and storage of a hazardous mineral acid such as hydrogen fluoride. Minimizing the process requirements also minimizes on-site inventory requirements and results in a substantial reduction in the risk that a serious accident might occur.

In a particularly preferred embodiment, the alkylation acid catalyst comprising HF acid and a cationic or anionic surfactant having $C_7$ or smaller aliphatic groups is combined with the olefinic and paraffinic feed hydrocarbons as hereinbefore described in an alkylation reaction zone. The reaction conditions can vary in temperature from sub-zero temperatures to temperatures as high as 95° C., and can be carried out at pressures varying from atmospheric to as high as 68 atmospheres and higher. The reaction products comprising the essentially refractory catalyst, unreacted feed hydrocarbons and reaction products formed in the alkylation reactor are next passed through a reaction soaker.

In the description of the preferred embodiments herein provided, it is intended that both the alkylation reactor and a reaction soaker, if one is utilized, are included within the scope of the term "alkylation reaction zone". Suitable reaction soakers are well known in the art. For example, the reaction soakers described in U.S. Pat. Nos. 3,560,587 and 3,607,970 may suitably be employed in the present process. Such reaction soakers are conventionally vessels equipped with perforated trays, baffle sections, packed beds, or high surface area contacting materials such as polymeric sheets or the like to maintain an alkylation reaction mixture in the form of a fairly homogeneous mixture, or emulsion, for a predetermined length of time. The alkylation reaction mixture of acid catalyst and hydrocarbons is maintained in the reaction soaker for a time which depends on the composition of the reaction mixture. Generally, a reaction soaker residence time of about 1 minute to about 30 minutes is employed. The temperature and pressure maintained in the reaction soaker are substantially the same as the temperature and pressure maintained in the associated alkylation reactor.

Means for settling the reaction mixture effluent from the alkylation reaction zone in order to separate a settled hydrocarbon phase and an acid catalyst phase are well known in the alkylation art. Generally, the effluent alkylation reaction mixture recovered from an alkylation reactor or soaker comprises a mixture of unreacted isoparaffins, alkylation reaction products, and the acid catalyst, said catalyst containing HF acid and a cationic or anionic sufactant, and catalyst-soluble organic materials possibly with small amounts of light hydrocarbons, etc. When this alkylation reaction mixture is allowed to stand unstirred, i.e., settled, the alkylation reaction hydrocarbon feed and products, isoparaffins and light hydrocarbons quickly form a lighter settled hydrocarbon phase. The acid catalyst phase comprising HF acid and the cationic or anionic surfactant component forms a separate phase. The settled hydrocarbon phase is then simply mechanically separated from the acid catalyst phase. The temperature and pressure maintained during such a settling operation are substantially the same as those described above in connection with the alkylation conditions employed in the reaction zone. The hydrocarbons and the catlyst are preferably in the liquid phase during the settling separation operation.

Some means for withdrawing heat from the alkylation zone may be necessary for optimum operation of the process. A variety of means for accomplishing the heat withdrawal are well known. For example, the heat generated in the alkylation reaction may be withdrawn from the alkylation reactor by indirect heat exchange between cooling water and the reaction mixture in the reactor.

In order to demonstrate the benefits and advantages of the present invention in contrast to prior art alkylation methods, the following examples are offered. It is to be understood that these examples are intended to be illustrative and in no way restrictive on the otherwise broad embodiments of the present invention as set forth in the claims appended hereto.

EXAMPLE I

This example was conducted in a pilot plant scale unit operation. The pilot plant comprised a monel autoclave in which the isoparaffin and olefin-acting agent are contacted with the hydrofluoric acid catalyst. After sufficient time, the hydrocarbon and acid phases are removed from the autoclave and passed to a settler in which the phases are allowed to separate. The acid phase is then removed from the settler and recycled back to the autoclave for contact with more hydrocarbon. The hydrocarbon phase comprising alkylate is removed from the settler and passed to neutralization facilities. Thereafter, the hydrocarbon phase is collected for analysis.

In this example, eight different runs were made in the pilot plant. The first run employed a 100% hydrofluoric acid catalyst. The seven subsequent runs employed 1 wt.% of a cationic surfactant and 99 wt.% HF acid as the circulating acid catalyst. Table I below relates the run number to the surfactant tested.

TABLE I

| Run # | Surfactant Type | Surfactant Tested |
|---|---|---|
| 1 | — | HF acid only |
| 2 | Cationic | Tetrabutylphosphonium Bromide |
| 3 | Cationic | Na mono- and didecyldisulfonated diphenyloxide |
| 4 | Anionic | Diisobutylthiophosphinate |
| 5 | Cationic | ($C_{10}$-$C_{18}$)2, Me, ClbenzylNCl |
| 6 | Cationic | ($C_{10}$-$C_{18}$), Me, (Clbenzyl)2NCl |
| 7 | Anionic | FC-170C-fluorinated alkyl alkoxylate |
| 8 | Anionic | FC-430-perfluoroalkyl sulfonate |

All the surfactants screened were either cationic or anionic surfactants. The surfactants used in Runs 2 and 4 contain alkyl groups of 4 carbon atoms. The surfactant used in Run 3 contains $C_{10}$ alkyl groups. The surfactants used in Runs 5-8 contain $C_{10}$-$C_{18}$ alkyl groups or mixtures of $C_{10}$-$C_{18}$ alkyl groups. The surfactants used in Runs 7 and 8 are produced by the 3M Company, with the name given being a tradename. In all runs, the conditions within the autoclave were the same and comprised a temperature of 20° C., a pressure of 8.8 atm., a residence time of 10 minutes, and a stirring rate of 1800 rpm. The volumetric ratio of olefin feed rate to the acid phase feed rate was held at 2.7. The mole ratio of isobutane to $C_4$ olefins was 7.5. The $C_4$ olefin molar distribution was 46.9% 2-butene, 34.8% 1-butene, and 28.3% isobutylene.

In each run, the alkylate product was analyzed and the products were found to have the following compositions and research octane numbers as set forth in Table II below.

TABLE II

| Conditions | Feedstock |
|---|---|
| Temp. - 20° C. | i-$C_4$/$C_4^=$ (mole/mole) = 7.5 |
| Pressure - 8.85 atm | $C_4^=$-2/$C_4^=$-1/i-$C_4^=$ = 46.9/34.8/28.3 (mol. %) |
| Stirring Rate - 1800 rpm | $C_4^=$/acid catalyst (vol/vol) = 2.7 |

| Run | Alkylate Yield (wt. %) | $C_8^-$ | TMP | DMH | $C_8^+$ | RON |
|---|---|---|---|---|---|---|
| 1 | 99.8 | 6.7 | 72.0 | 17.2 | 4.1 | 92.7 |
| 2 | 98.9 | 6.3 | 76.6 | 15.5 | 5.6 | 93.4 |
| 3 | 99.9 | 7.3 | 72.3 | 15.1 | 5.5 | 93.5 |
| 4 | 99.5 | 6.6 | 74.6 | 14.6 | 4.2 | 93.9 |
| 5 | 99.5 | 6.6 | 71.6 | 16.9 | 4.9 | 92.8 |
| 6 | 99.7 | 6.5 | 72.4 | 17.0 | 4.1 | 92.8 |
| 7 | 99.6 | 6.8 | 70.8 | 17.3 | 5.1 | 92.7 |
| 8 | 99.5 | 6.4 | 74.0 | 16.8 | 2.8 | 93.3 |

The research octane numbers reported above were calculated by hand based upon gas chromatograph data. The octane results have an accuracy of ±0.2 RON.

From the results as set forth in Table II, it is evident that the addition of cationic or anionic surfactants containing $C_{10}$ or smaller alkyl groups are most useful in improving the octane of an HF acid catalyzed alkylation reaction zone producing a process operating at a high olefin to acid volumetric feed ratio. This conclusion becomes more evident when comparing the TMP (trimethylpentane) to DMH (dimethylhexane) weight ratio of each run as set forth in Table III below.

TABLE III

| Run # | TMP/DMH (wt/wt) |
|---|---|
| 1 | 4.18 |
| 2 | 4.68 |
| 3 | 4.79 |
| 4 | 5.10 |
| 5 | 4.24 |
| 6 | 4.25 |
| 7 | 4.09 |
| 8 | 4.40 |

The ratios listed above are a comparison of the weight of high octane (103 RON average) trimethylpentane compounds to low octane (70 RON average) dimethylhexane compounds. Thus the larger the ratio, the greater the expected Research Octane Number (RON) of the product alkylate. It can be clearly seen from the results in Table III that the surfactants tested which contained $C_{10}$ or smaller aliphatic or aromatic substituted components (Runs 2-4) are most effective in improving the alkylate quality of a low acid alkylation process. The surfactants tested containing aliphatic or aromatic substituted components larger than $C_{10}$ only marginally improve the product octane when compared to the straight HF acid case of Run 1.

EXAMPLE II

The following example illustrates the effect that the olefin to acid feed ratio has on motor alkylate quality. In this example, additional autoclave pilot plant runs were completed utilizing varying olefin to acid feed ratios. The olefin to acid feed ratios were varied utilizing HF acid catalyst only, and also utilizing the anionic surfactant diisobutylthiophosphinate. Diisobutylthiophosphinate has the chemical formula:

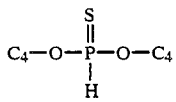

Diisobutylthiophosphinate contains only $C_4$ aliphatic substituted components and was determined in Example I to be the most useful anionic surfactant of the seven surfactants screened.

The autoclave pilot plant utilized for the runs of this example is identical to that utilized in the first example. The operating conditions utilized are also the same and consisted of a temperature 20° C., a pressure of 8.8 atm, a residence time of 10 minutes, and a stirring rate of 1800 rpm. The results of five runs can be found in Table IV below.

TABLE IV

| Conditions | Feedstock | | | | |
|---|---|---|---|---|---|
| Temp. - 20° C. | i-$C_4$/$C_4^=$ (mole/mole) = 7.5 | | | | |
| Pressure - 8.85 atm | $C_4^=$—2/$C_4^=$—1/$iC_4^=$ = 46.9/34.8/28.3 (mol. %) | | | | |
| Stirring Rate - 1800 rpm | | | | | |

| Modifier (wt. %) | HF Acid Only | | | HF Acid (99 wt. %) Diisobutylthiophos- phinate (1 wt. %) | |
|---|---|---|---|---|---|
| $C_4^=$ olefin/HF acid (v/v) | 0.08 | 2.7 | 10.8 | 2.7 | 10.8 |
| Alkylate Yield (wt. %) | 99.9 | 99.8 | 99.6 | 99.5 | 99.7 |
| Alkylate Comp. (wt. %) | | | | | |
| $C_8^-$ | 9.6 | 6.7 | 7.1 | 6.6 | 6.9 |
| TMP | 71.7 | 72.0 | 71.1 | 74.6 | 74.3 |
| DMH | 13.9 | 17.2 | 17.2 | 14.6 | 14.5 |
| $C_8^+$ | 4.7 | 4.1 | 4.6 | 4.2 | 4.3 |
| TMP/DMH (m/m) | 5.16 | 4.19 | 4.13 | 5.11 | 5.12 |
| RON | 93.8 | 92.7 | 92.3 | 93.9 | 93.8 |

The results as set forth in the above table indicate that product octane decreases with increasing olefin to acid volumetric feed ratio in a process catalyzed by HF acid only. When diisobutylthiophosphinate, an anionic surfactant, is used to promote the reaction, product octanes equivalent to an HF acid only system employing an olefin to acid ratio over 100 times less than that employed in the anionic surfactant promoted case are produced. Additionally, product octanes in the promoted catalyst case vary insignificantly with a large increase in olefin to acid volumetric feed ratios.

What is claimed is:

1. A process for the liquid phase alkylation of an isoparaffin with an olefin acting agent at alkylation reaction conditions including an olefin to acid catalyst volumetric feed ratio greater than 1.0 wherein the acid catalyst comprises from 95.0 to 99.5 wt.% hydrofluoric acid and from 0.5 to 5.0 wt.% of a cationic or anionic surfactant containing a sulfur component in the form of sulfated esters, sulfated alkanolamides, alkyl sulfates and sulfonates, or a phosphorous component selected from the group alkylphosphates, alkylpolyphosphates, monoester phosphates, and diesterphosphates wherein the surfactant contains no aliphatic or aromatic groups having more than 7 carbon atoms.

2. The process of claim 1 further characterized in that the anionic surfactant is diisobutylthiophosphinate.

3. The process of claim 1 further characterized in that the cationic surfactant is tetrabutylphosphonium bromide.

4. A process for the liquid phase alkylation of isobutane with $C_4$ olefins at alkylation reaction conditions including a temperature of from 0° to 95° C., a pressure of from 1 to 50 atmospheres, and a $C_4$ olefin to acid catalyst volumetric feed ratio greater than 1.0 wherein the acid catalyst is comprised of from 95.0 to 99.5 wt.% hydrofluoric acid and from 0.5 to 5.0 wt.% of an anionic surfactant containing a sulfur component selected from the group of sulfated esters, sulfated alkanolamides, alkyl sulfates and sulfonates or a phosphorous component selected from the group alkylphosphates, alkylpolyphosphates, monoesterphosphates, and diesterphosphates wherein the surfactant contains no aliphatic or aromatic groups having more than 7 carbon atoms.

5. The process of claim 4 further characterized in that the anionic surfactant component is diisobutylthiophosphinate.

* * * * *